United States Patent [19]

Effland et al.

[11] Patent Number: 5,204,480

[45] Date of Patent: Apr. 20, 1993

[54] 5-(1-HYDROXYLCYCLOALKYL)-2-METHOXY PYRIDINE COMPOUNDS

[75] Inventors: Richard C. Effland, Bridgewater, N.J.; David M. Fink, Doylestown, Pa.

[73] Assignee: Hoechst-Roussel Pharmaceuticals Inc., Somerville, N.J.

[21] Appl. No.: 838,983

[22] Filed: Feb. 21, 1992

Related U.S. Application Data

[62] Division of Ser. No. 710,472, Jun. 5, 1991, Pat. No. 5,112,981, which is a division of Ser. No. 594,496, Oct. 9, 1990, Pat. No. 5,039,809, which is a division of Ser. No. 394,448, Aug. 16, 1989, Pat. No. 4,978,663.

[51] Int. Cl.$^5$ .......................................... C07D 213/64
[52] U.S. Cl. ........................................ 546/344; 544/82; 544/130; 544/131; 546/14; 546/187; 546/194; 546/281; 546/291; 546/300; 546/301
[58] Field of Search ................................... 546/344

[56] References Cited

U.S. PATENT DOCUMENTS 3,716,543  2/1973  Hall ................................. 546/344

Primary Examiner—C. Warren Ivy
Assistant Examiner—James H. Turnipseed
Attorney, Agent, or Firm—Tatsuya Ikeda

[57] ABSTRACT

There are described compounds of the formula

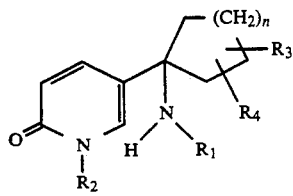

where
n is 1, 2 or 3;

$R_1$ is hydrogen, formyl, loweralkylcarbonyl, aryl-loweralkylcarbonyl, loweralkyl, arylloweralkyl,

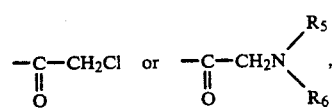

$R_5$ and $R_6$ being independently loweralkyl or alternatively the group

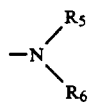

taken as a whole is

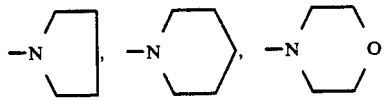

or

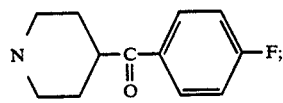

$R_2$ is hydrogen, loweralkyl, loweralkenyl, aryllower-alkyl, —CH$_2$C≡CH,

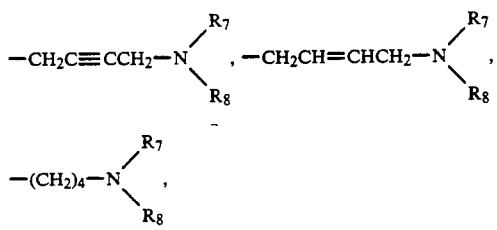

$R_7$ and $R_8$ being independently loweralkyl or alternatively the group

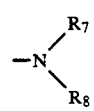

taken as a whole is

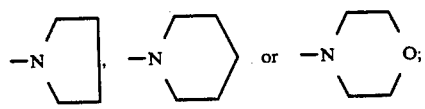

$R_3$ is hydrogen is loweralkyl; and
$R_4$ is hydrogen or loweralkyl;

which compounds are useful as analgesic agents and also for treating various memory dysfunctions.

5 Claims, No Drawings

5-(1-HYDROXYLCYCLOALKYL)-2-METHOXY PYRIDINE COMPOUNDS

This is a division of a prior application, Ser. No. 710,472, filed Jun. 5, 1991, now U.S. Pat. No. 5,112,981, which is a division of a prior application, Ser. No. 594,496, filed Oct. 9, 1990, now U.S. Pat. No. 5,039,809, which is a division of a prior application, Ser. No. 394,448, filed Aug. 16, 1989, now U.S. Pat. No. 4,978,663.

This invention relates to compounds having the formula

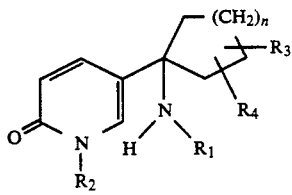

where
n is 1, 2 or 3;
$R_1$ is hydrogen, formyl, loweralkylcarbonyl, aryl-loweralkylcarbonyl, loweralkyl, arylloweralkyl,

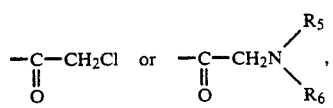

$R_5$ and $R_6$ being independently loweralkyl or alternatively the group

taken as a whole is

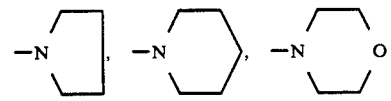

or

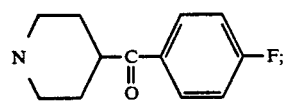

$R_2$ is hydrogen, loweralkyl, loweralkenyl, arylloweralkyl, —CH$_2$C≡CH,

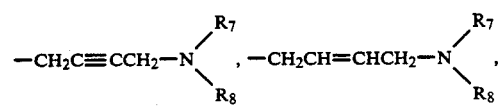

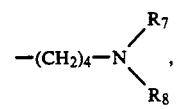

$R_7$ and $R_8$ being independently loweralkyl or alternatively the group

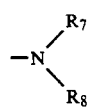

taken as a whole is

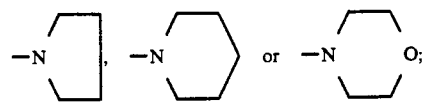

$R_3$ is hydrogen or loweralkyl; and
$R_4$ is hydrogen or loweralkyl;
which compounds are useful as analgesic agents and also for treating various memory dysfunctions.

Also included within the scope of this invention are compounds of Formulas II and III where $R_9$ is hydrogen, loweralkyl or arylloweralkyl which compounds are useful as direct precursors of the target compounds of this invention.

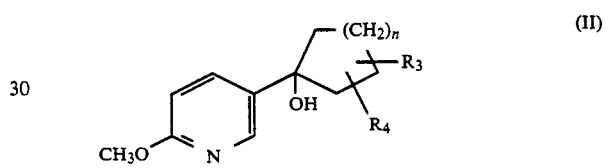

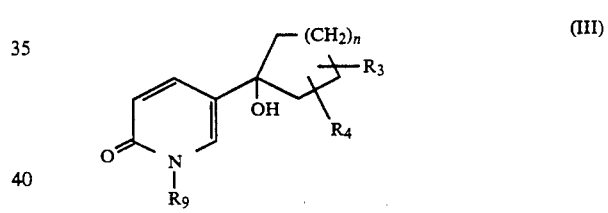

Throughout the specification and the appended claims, a given chemical formula or name shall encompass all stereo, geometrical and optical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

The term loweralkenyl shall mean a straight or branched alkenyl group having from 1 to 6 carbon atoms and only one carbon-carbon double bond. Said double bond shall not be at the alpha-position with respect to the position where the loweralkenyl substituent is located.

Unless otherwise stated or indicated, the term halogen shall mean fluorine, chlorine, bromine or iodine.

Unless otherwise stated or indicated, the term aryl shall mean a phenyl group optionally mono-substituted with a loweralkyl, loweralkoxy, halogen or trifluoromethyl group.

The compounds of this invention are prepared by utilizing one or more of the synthetic steps described below.

Throughout the description of the synthetic steps, the definitions of n and $R_1$ through $R_9$ are as given above unless otherwise stated or indicated, and other nomenclatures shall have their respective meanings given in their first appearances.

STEP A

5-Bromo-2(1H)-pyridinone is allowed to react with triisopropylsilyl-trifluoromethanesulfonate to afford 5-bromo-2-(triisopropylsilyloxy)pyridine having the formula IV.

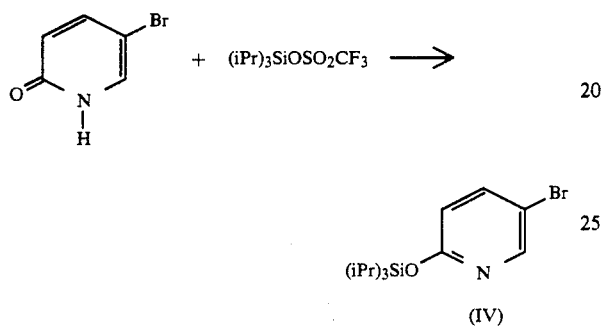

The above reaction is typically conducted in the presence of a suitable acid scavenger such as 2,6-dimethylpyridine and a suitable solvent such as dichloromethane at a temperature of about 0° to 25° C.

STEP B

Compound IV is allowed to react with n-BuLi and thereafter the resultant anion is allowed to react with a cyclic ketone of Formula V to afford a compound of Formula VI.

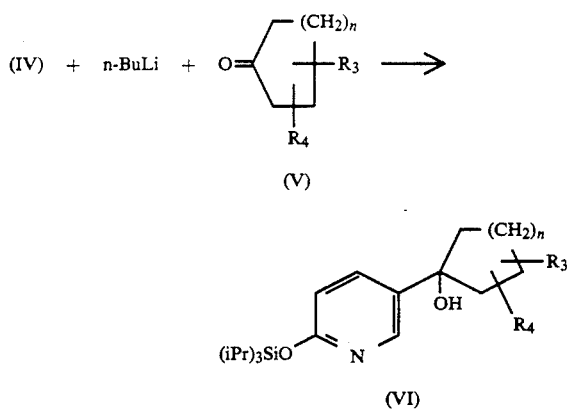

The reaction between compound IV and n-BuLi is typically conducted in a suitable solvent such as diethyl ether at a temperature of about −78° to 0° C. The subsequent reaction between the resultant complex and compound V is typically conducted in the same solvent at a temperature of about −78° to 25° C.

STEP C

Compound VI is allowed to react with hydrofluoric acid to afford a compound of Formula VII.

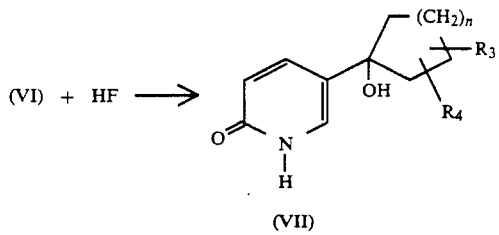

The above reaction is typically conducted by adding an aqueous solution of HF to a solution of compound VI in a suitable solvent such as acetonitrile and stirring the resultant mixture at a temperature of about 0° to 25° C.

STEP D

Compound VII is allowed to react with a halide compound of the formula $R_{10}$-Hal, where Hal is chlorine, bromine, or iodine and $R_{10}$ is loweralkyl or arylloweralkyl, in a routine manner known to the art to afford a compound of Formula VIII.

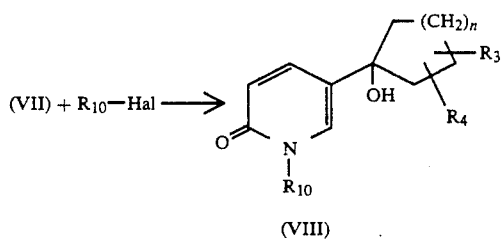

As an alternative to the foregoing STEPS A through D, one can also utilize STEPS E and F described below.

STEP E

5-Bromo-2-methoxypyridine is allowed to react with n-BuLi and thereafter the resultant anion is allowed to react with compound V in substantially the same manner as in STEP B to afford a compound of Formula IX.

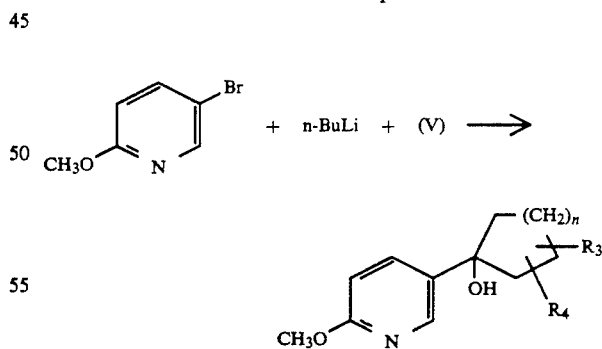

STEP F

Compound IX is allowed to react with a halide compound of the formula $R_{10}$-Hal where Hal is bromine or iodine to afford compound VIII.

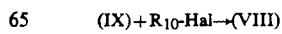

The above reaction is typically conducted in the presence of an inorganic base such as potassium carbonate and a suitable medium such as acetonitrile at a temperature of about 60° to 85° C.

STEP G

A compound of Formula X which is obtained from STEP C, D or F is allowed to undergo Ritter reaction with HCN whereby the tertiary —OH group of compound X is converted to a —NHCHO group to afford a compound of Formula XI.

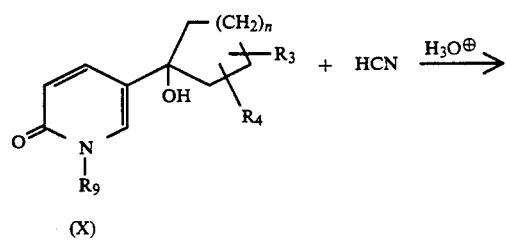

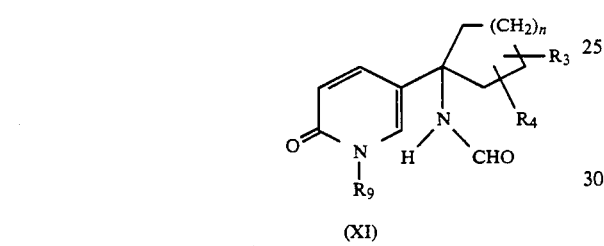

Typically, the above reaction is conducted in the presence of potassium cyanide, trifluoroacetic acid and concentrated sulfuric acid at a temperature of about 0° to 25° C.

STEP H

Compound X is allowed to undergo Ritter reaction with a nitrile compound of the formula $R_{11}$-CN where $R_{11}$ is loweralkyl to afford a compound of Formula XII.

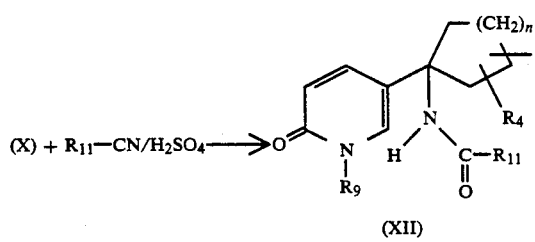

Typically, the above reaction is conducted in the presence of concentrated sulfuric acid. Optionally, the nitrile $R_{11}CN$ or trifluoroacetic acid may be used as a cosolvent. Typically, the reaction is conducted at a temperature of about 0° to 25° C.

STEP I

Compound XI is reduced with NaBH₄ to afford a compound of Formula XIII.

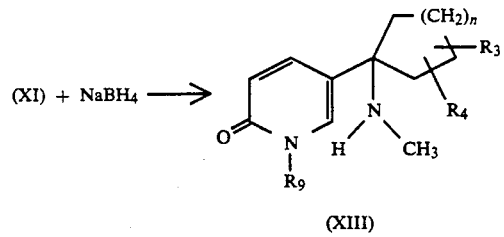

Typically, the above reaction is conducted in a suitable medium such as a mixture of acetic acid and tetrahydrofuran at a temperature of about 50° to 65° C.

STEP J

Compound XI is hydrolyzed to afford a compound of Formula XIV.

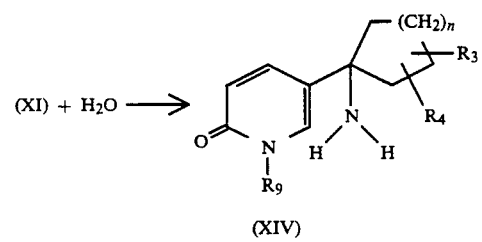

The above reaction is typically conducted in the presence of hydrochloric acid and methanol at a temperature of about 25° to 65° C.

STEP K

Compound XIV is allowed to react with an acid anhydride of the formula

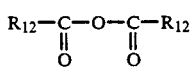

where $R_{12}$ is loweralkyl or arylloweralkyl, or with an acid halide of the formula

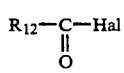

where Hal is chlorine or bromine to afford a compound of Formula XV.

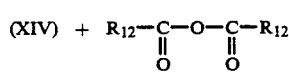

or

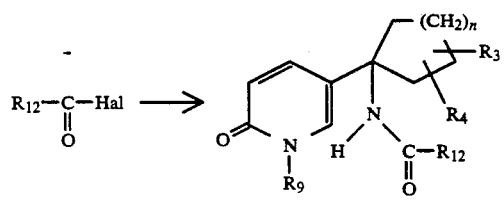

The above reaction is typically conducted in the presence of an acid scavenger such as triethylamine and a suitable solvent such as dichloromethane at a temperature of about 0° to 25° C.

STEP L

A compound of Formula XIVa obtained from STEP J is allowed to react preferably with about two molar equivalents of a compound of the formula $$Ar-\underset{\underset{O}{\|}}{C}-O-\underset{\underset{O}{\|}}{C}-Ar \quad \text{or} \quad Ar-\underset{\underset{O}{\|}}{C}-Hal,$$

where Ar is an aryl group and Hal is chlorine or bromine, to afford a compound of Formula XVI.

(XIVa structure) + Ar-C(=O)-O-C(=O)-Ar (XIVa)

or Ar—C(=O)—Hal (2 eq.) →

(XVI structure)

(XVI)

The novel compounds of Formula XVI are within the scope of this invention.

STEP M

Compound XVI is hydrolyzed to afford a compound of Formula XVII.

(XVI) + H$_2$O → (XVII structure)

(XVII)

This hydrolysis is typically conducted with the aid of an acid and a solvent which are similar to those used in STEP J.

STEP N

Compound XIVa is allowed to react with triisopropylsilyltrifluoromethanesulfonate in substantially the same manner as in STEP A and thereafter the resultant product is allowed to react with chloroacetic anhydride to afford a compound of Formula XVIII.

$$\text{(XIVa)} \xrightarrow[\text{(2) ClCH}_2-\underset{\underset{O}{\|}}{C}-O-\underset{\underset{O}{\|}}{C}-CH_2Cl]{\text{(1) (iPr)}_3\text{SiOSO}_2\text{CF}_3}$$

(XVIII structure)

(XVIII)

The second reaction mentioned above is typically conducted in the presence of poly(4-vinylpyridine) and a catalytic amount of N,N-dimethyl-4-aminopyridine as well as a suitable solvent such as dichloromethane at a temperature of about 0° to 25° C.

STEP O

Compound XVIII is allowed to react with a tertiary amine of the formula $$H-N\underset{R_6}{\overset{R_5}{\diagdown}}$$

to afford a compound of Formula XIX.

(XVIII) + H—N(R$_5$)(R$_6$) →

(XIX structure)

(XIX)

The above reaction is typically conducted in the presence of a tertiary amine such as diisopropylethylamine and a suitable solvent such as acetonitrile at a temperature of about 50° to 65° C.

STEP P

A compound of Formula XIa obtained from STEP G is allowed to react with BrCH$_2$C≡CSi(CH$_3$)$_3$ to afford a silyl compound of Formula XX. This reaction is typically conducted in the presence of an inorganic base such as K$_2$CO$_3$ and a suitable solvent such as dimethylformamide at a temperature of about 25° to 50° C.

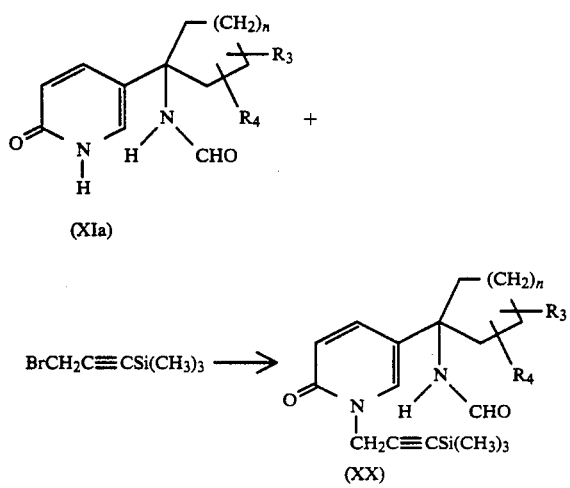

(XIa)

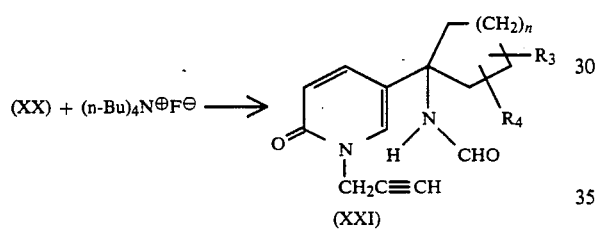

(XX)

Subsequently, compound XX is allowed to react with tetra-n-butylammonium fluoride to afford a compound of Formula XXI. This reactions is typically conducted in the presence of a suitable solvent such as tetrahydrofuran at a temperature of about 0° to 25° C.

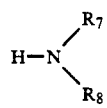

(XXI)

STEP Q

Compound XXI is allowed to react with paraformaldehyde and a secondary amine of the formula $$H-N\begin{matrix}R_7\\R_8\end{matrix}$$

to afford a compound of Formula XXII (Mannich reaction). This reaction is typically conducted in the presence of cuprous chloride and a suitable solvent such as dioxane at a temperature of about 25° to 80° C.

(XXI) + HCHO + H—N$\begin{matrix}R_7\\R_8\end{matrix}$ →

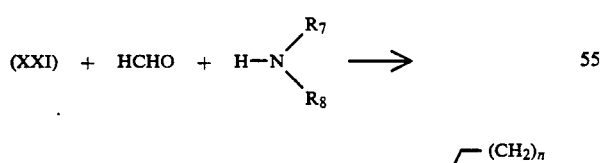

(XXII)

STEP R

Compound XXII is hydrolyzed in substantially the same manner as in STEP J to afford a compound of Formula XXIII.

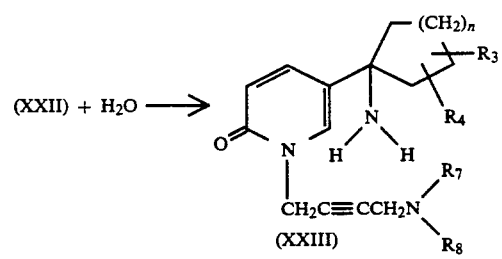

(XXIII)

STEP S

One of the primary amino hydrogens of compound XXIII can be converted to various other functional groups falling within the definition of $R_1$ by utilizing STEPS K, L, M, N and/or O described above.

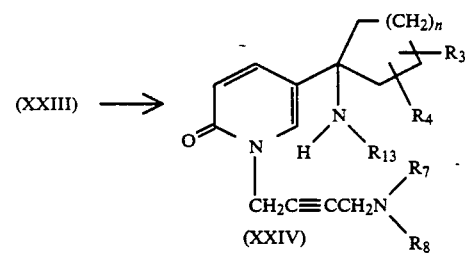

(XXIV)

$R_{13}$ = loweralkylcarbonyl, arylloweralkylcarbonyl, loweralkyl, arylloweralkyl or $-\underset{\underset{O}{\|}}{C}-CH_2N\begin{matrix}R_5\\R_6\end{matrix}$

STEP T

A compound of Formula XXV obtained by utilizing one or more of the foregoing steps is catalytically hydrogenated to afford a compound of Formula XXVI. This hydrogenation is typically conducted with the aid of a suitable catalyst such as Pd on BaSO$_4$ and a suitable medium such as methanol at a temperature of about 25° to 50° C.

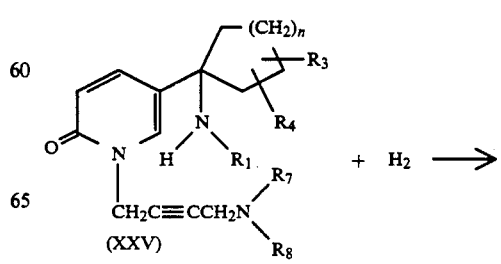

(XXV)      + H$_2$ →

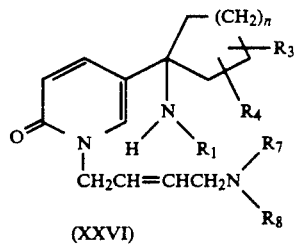

(XXVI)

STEP U

Compound XXVI is catalytically hydrogenated to afford a compound of Formula XXVII. This hydrogenation is typically conducted with the aid of a suitable catalyst such as Pd on carbon and a suitable medium such as ethanol at a temperature of about 25° to 40° C.

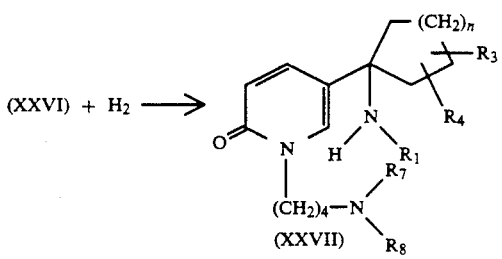

The compounds of Formula I of the present invention are useful as analgesic agents due to their ability to alleviate pain in mammals. The activity of the compound is demonstrated in the 2-phenyl-1,4-benzoquinone-induced writhing test in mice, a standard assay for analgesia [Proc. Soc. Exptl. Biol. Med., 95,729 (1957)]. Table 1 shows results of the test for of some of the compounds of this invention.

TABLE 1

| Compound | ANALGESIC ACTIVITY (Phenylquinone Writhing) Analgesic PQW, % Inhibition of Writhing at 20 mg/kg, s.c. |
|---|---|
| cis-N-[1-(1,6-Dihydro-1-methyl-6-oxo-3-pyridinyl)-4-(1,1-dimethylethyl)cyclohexyl]acetamide | 47% |
| 5-(1-Amino-4,4-dimethylcyclohexyl)-2(1H)-pyridinone hydrochloride | 62% |
| 5-(1-Aminocyclohexyl)-1-(phenylmethyl)-2(1H)-pyridinone hydrochloride | 42% |
| N-[1-(1,6-Dihydro-6-oxo-3-pyridinyl)cyclohexyl][4-(4-fluorobenzoyl)]-1-piperidineacetamide | 77% |
| N-[1-(1,6-Dihydro-6-oxo-3-pyridinyl)cyclohexyl]acetamide | 58% |
| N-[1-(1,6-Dihydro-6-oxo-3-pyridinyl)cyclohexyl]benzamide | 72% |
| 5-(1-Aminocyclohexyl)-1-[4-(pyrrolidin-1-yl)-2-butynyl]-2(1H)-pyridinone (Reference Compound) | 53% |
| Propoxyphene | 50% at 3.9 mg/kg, s.c. |

The compounds of Formula (I) of the present invention can also be used for the treatment of various memory dysfunctions such as Alzheimer's disease.

This utility can be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of Dark Avoidance Assay for representative compounds of this invention and a reference compound are presented in Table 3.

TABLE 2

| Compound | Dark Avoidance Assay | |
|---|---|---|
| | Dose mg/kg, s.c. | % of animals with scopolamine induced memory deficit reversal |
| 5-(1-Aminocyclohexyl)-1-(phenylmethyl)-2(1H)-pyridinone hydrochloride | 0.16 | 20% |
| 5-(1-Amino-4,4-dimethylcyclohexyl)-2(1H)-pyridinone hydrochloride | 2.5 | 20% |
| cis-N-[1-(1,6-Dihydro-1-methyl-6-oxo-3-pyridinyl)-4-(1,1-dimethylethyl)cyclohexyl]-acetamide | 1.3 | 33% |
| N-[1-(1,2-Dihydro-1-methyl-2-oxo-5-pyridinyl)cyclohexyl]-acetamide | 0.63 | 33% |
| Physostigmine (Reference) | 0.31 | 20% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include
N-[1-(1,6-Dihydro-6-oxo-3-pyridinyl)cyclohexyl]formamide;
N-[1-(1,6-Dihydro-6-oxo-3-pyridinyl)-4,4-dimethylcyclohexyl]formamide;
N-[1-(1,6-Dihydro-1-methyl-6-oxo-3-pyridinyl)cyclohexyl]acetamide;
cis-N-[1,6-Dihydro-1-methyl-6-oxo-3-pyridinyl)-4-(1,1-dimethylethyl)-cyclohexyl]acetamide;
N-[1-[1,6-Dihydro-6-oxo-1-(phenylmethyl)-3-pyridinyl]cyclohexyl]formamide;
5-(1-Aminocyclohexyl)-2(1H)-pyridinone;
5-(1-Amino-4,4-dimethylcyclohexyl)-2(1H)-pyridinone;
5-(1-Aminocyclohexyl)-1-methyl-2(1H)-pyridinone;
5-(1-Aminocyclohexyl)-1-(phenylmethyl)-2(1H)-pyridinone;
N-[1-(1,6-Dihydro-6-oxo-3-pyridinyl)cyclohexyl]benzamide;
N-[1-(1,6-Dihydro-6-oxo-3-pyridinyl)cyclohexyl]acetamide;
N-[1-(1,6-Dihydro-6-oxo-3-pyridinyl)cyclohexyl]propionamide;
N-1-[1,6-Dihydro-1-methyl-6-oxo-3-pyridinyl]cyclohexyl]benzeneacetamide;
N-[1-[1,6-Dihydro-6-oxo-1-(phenylmethyl)-3-pyridinyl]cyclohexyl]benzeneacetamide;
N-[1-(1,6-Dihydro-6-oxo-3-pyridinyl)cyclohexyl]chloroacetamide;
N-[1-(1,6-Dihydro-6-oxo-3-pyridinyl)cyclohexyl][4-(4-fluorobenzoyl)]-1-piperidineacetamide;
5-[1-(Methylamino)cyclohexyl]-1-methyl-2(1H)-pyridinone;
5-[1-(Methylamino)cyclohexyl]-1-(phenylmethyl)-2(1H)-pyridinone;
N-[1-[1,6-Dihydro-6-oxo-1-(2-propynyl)-3-pyridinyl]cyclohexyl]formamide;
5-(1-Aminocyclohexyl)-1-[4-(pyrrolidin-1-yl)-2-butynyl]-2(1H)-pyridinone;
N-[1-[6-(Benzoyloxy)-3-pyridinyl]cyclohexyl]benzamide;
5-(1-Hydroxycyclohexyl)-2(1H)-pyridinone;
5-(4,4-dimethyl-1-hydroxycyclohexyl)-2(1H)-pyridinone;
5-(1-Hydroxycyclohexyl)-1-methyl-2(1H)-pyridinone;
5-[4-(1,1-Dimethylethyl)-1-hydroxycyclohexyl]-1-methyl-2(1H)-pyridinone;
5-(1-Hydroxycyclohexyl)-1-(phenylmethyl)-2(1H)-pyridinone;
5-(1-Hydroxycyclohexyl)-2-methoxypyridine;
5-[4-(1,1-Dimethylethyl)-1-hydroxycyclohexyl]-2-methoxypyridine;

The following examples are presented in order to illustrate this invention.

EXAMPLE 1

5-Bromo-2-(triisopropylsilyloxy)pyridine

Triisopropylsilyl trifluoromethanesulfonate (65.4 g) was added dropwise to a solution of 5-bromo-2(1H)-pyridinone (33.8 g) and 2,6-lutidine (31.1 g) in 775 ml of dichloromethane at 0° C. The resulting solution was stirred for 15 minutes, and then it was poured into water and the layers were separated. The aqueous phase was extracted with dichloromethane, and the combined organic layers were dried over magnesium sulfate and concentrated to give a liquid. The product was slurried with silica gel and hexanes. Filtration gave 64.6 g of oil.

EXAMPLE 2

5-(1-Hydroxycyclohexyl)-2(1H)-pyridinone

A solution of n-butyllithium (2.5M in hexanes, 92 ml) was added dropwise over 50 minutes to a solution of 5-bromo-2-triisopropylsilyloxypyridine (69.0 g) in 800 ml of diethyl ether at −40° to −45° C. The resulting solution was stirred at −40° to −45° C. for 0.5 hour, and then cyclohexanone (22.5 g) in 25 ml of diethyl ether was added dropwise. The mixture was allowed to warm to 0° C., quenched with saturated ammonium chloride solution, and extracted with diethyl ether. The combined organic phases were washed with saturated sodium chloride solution, dried over magnesium sulfate, filtered and concentrated to give 79 g of crude product as an oil.

The product formed above was dissolved in 260 ml of acetonitrile at 0° C., and hydrofluoric acid (48% in water, 7.1 ml) was added rapidly, dropwise. The thick suspension was stirred for 5 minutes, and then the precipitated product was collected by filtration, yielding 29.0 g of 5-(1-hydroxycyclohexyl)-2(1H)-pyridinone as a powder. An analytical sample was obtained by recrystallization from methanol/diethyl ether, m.p. 194°–196° C.

ANALYSIS: Calculated for $C_{11}H_{15}NO_2$: 68.37%C; 7.82%H; 7.25%N. Found: 68.46%C; 7.72%H; 7.23%N.

EXAMPLE 3

5-(4,4-Dimethyl-1-hydroxycyclohexyl-2(1H)-pyridinone

A solution of n-butyllithium (1.6M in hexanes, 132 ml) was added dropwise over 50 minutes to a solution of 5-bromo-2-triisopropylsilyloxypyridine (63.6 g) in 750 ml of diethyl ether at −45° to −40° C. The resulting solution was stirred at −45° to −40° C. for 0.5 hour, and then 4,4-dimethylcyclohexanone (26.5 g) in 50 ml of diethyl ether was added dropwise. The mixture was allowed to warm to 0° C., quenched with saturated ammonium chloride solution, and extracted with diethyl ether. The combined organic phases were washed with saturated sodium chloride solution, dried over magnesium sulfate, filtered, and concentrated to give 75 g of crude product as an oil.

The product formed above was dissolved in 260 ml of acetonitrile at 0° C., and hydrofluoric acid (48% in water, 7.1 ml) was added rapidly dropwise. The thick suspension was stirred for 5 minutes, and then the precipitated product was collected by filtration, yielding 26.0 of 5-(4,4-dimethyl-1-hydroxycyclohexyl)-2(1H)-pyridinone as a powder. An analytical sample was obtained by two recrystallizations from methanol, m.p. 210°–211° C.

ANALYSIS: Calculated for $C_{13}H_{19}NO$: 70.56%C; 8.65%H; 6.33%N. Found: 70.67%C; 8.70%H; 6.35%N.

EXAMPLE 4

5-(1-Hydroxycyclohexyl)-2-methoxypyridine

A solution of n-butyllithium (1.6M in hexanes, 150 ml) was added dropwise over 1 hour to a mechanically stirred solution of 5-bromo-2-methoxypyridine (39.3 g) in 800 ml of diethyl ether at −40° C. The resulting slurry was stirred at −40° C. to −45° C. for 45 minutes, and then cyclohexanone (23.5 g) in 50 ml of diethyl ether was added dropwise over 1 hour. The mixture was allowed to warm to 0° C. over about 1 hour, and then the reaction was quenched with saturated ammonium chloride solution. The layers were separated, and the aqueous phase was extracted with diethyl ether. The combined organic phases were washed with saturated sodium chloride solution, dried over magnesium sulfate, filtered and concentrated to yield a semi-solid material. Trituration with pentane provided 29.0 g of product as a powder. Recrystallization of 8 g of the product gave 6.2 g of plates, m.p. 74°–75° C.

ANALYSIS: Calculated for $C_{12}H_{17}NO_2$: 69.54%C; 8.27%H; 6.76%N. Found: 69.53%C; 8.37%H; 6.76%N.

EXAMPLE 5 cis/trans 5-[4-(1,1-Dimethylethyl)-1-hydroxycyclohexyl]-2-methoxypyridine

A solution of n-butyllithium (1.6M in hexanes, 100 ml) was added dropwise over 1 hour to a mechanically stirred solution of 5-bromo-2-methoxypyridine (40 g) in 800 ml of diethyl ether at −40° C. The resulting slurry was stirred at −40° C. to −45° C. for 45 minutes, and then 4-t-butyl cyclohexanone (39 g) in 240 ml of diethyl ether was added dropwise over 1.5 hours. The mixture was allowed to warm to 0° C. over 1 hour, and then the reaction was quenched with saturated ammonium chloride solution. The layers were separated, and the aqueous phase was extracted with diethyl ether. The combined organic phases were washed with saturated sodium chloride solution, dried over magnesium sulfate, filtered and concentrated to yield a semi-solid material. Trituration with pentane provided 29 g of powder as a mixture of epimers which was used in subsequent reactions without further purification.

EXAMPLE 6

5-(1-Hydroxycyclohexyl)-1-methyl-2(1H)-pyridinone

A mixture of 5-(1-hydroxycyclohexyl)-2-methoxypyridine (17.1 g), methyl iodide (11.7 g) and potassium carbonate (22.8 g) was heated in 330 mL of refluxing acetonitrile for 18 hours. The mixture was cooled and filtered, and the solids were washed with methanol. The filtrate was concentrated to yield 14.0 g of powder, which was used in subsequent reactions without further purification.

EXAMPLE 7 cis/trans-5-[4-(1,1-Dimethylethyl)-1-hydroxycyclohexyl]-1-methyl-2(1H)-pyridinone A mixture of cis/trans 5-[4-(1,1-dimethylethyl)-1-hydroxycyclohexyl]-2-methoxypyrridine (29.0 g), methyl iodide (15.6 g), and potassium carbonate (30.0 g) was heated in 440 mL of refluxing acetonitrile for 18 hours. The resulting suspension was cooled and filtered, and the solids were washed with methanol. The filtrate was concentrated to a small volume, and the precipitated product was collected to afford 32 g of powder, which was used in subsequent reactions without purification.

EXAMPLE 8

5-(1-Hydroxycyclohexyl)-1-(phenylmethyl)-2(1H)-pyridinone

A mixture of 5-(1-hydroxycyclohexyl)-2-methoxy pyridine (26.3 g), benzyl bromide (21.7 g) and potassium carbonate (35 g) was heated in 500 mL of refluxing acetonitrile for 17 hours. The mixture was cooled and filtered, and the solids were washed with methanol. The filtrate was concentrated to give 39.5 g of an oil. HPLC on silica gel (elution with ethyl acetate) afforded 20.8 g of solid.

EXAMPLE 9

N-[1-(1,6-Dihydro-6-oxo-3-pyridinyl)cyclohexyl] formamide hydrochloride

Concentrated sulfuric acid (150 ml) was added dropwise over 45 minutes to a suspension of 5-(1-hydroxycyclohexyl)-2(1H)-pyridinone (37.0 g) and potassium cyanide (370 g) in 770 ml of trifluoroacetic acid at 0° C. The resulting suspension was stirred at room temperature for 17 hours and then cooled to 0° C., and diethyl ether was added slowly. The solvent was decanted, and the solids were washed with diethyl ether. The product was then dissolved in methanol and neutralized with poly-4-vinylpyridine. The polymer was removed by filtration, and the filtrate was concentrated to yield a white foam, which was dissolved in methanol and acidified with ethereal HCl. The solvent was removed in vacuo to afford a foam (43.2 g) which was used in subsequent reactions without further purification.

EXAMPLE 10

N-[1-(1,6-Dihydro-6-oxo-3-pyridinyl)-4,4-dimethylcyclohexyl] formamide hydrochloride Concentrated sulfuric acid (54 ml) was added dropwise over 45 minutes to a suspension of 5-(4,4-dimethyl-1-hydroxycyclohexyl)-2(1H)-pyridinone (15 g) and potassium cyanide (13.2 g) in 272 ml of trifluoroacetic acid at 0° C. The resulting suspension was stirred at room temperature for 17 hours and then cooled to 0° C., and diethyl ether was added slowly. The solvent was decanted, and the solids were washed with diethyl ether. The product was then dissolved in methanol and neutralized with poly-4-vinylpyridine. The polymer was removed by filtration, and the filtrate concentrated, yielding a foam, which was dissolved in methanol and acidified with ethereal HCl. The volume of solvent was reduced in vacuo, and the precipitated solid (7.1 g) was collected and used in subsequent reactions without further purification.

EXAMPLE 11

N-[1-(1,6-Dihydro-1-methyl-6-oxo-3-pyridinyl)cyclohexyl]-acetamide

Concentrated sulfuric acid (40 ml) was added dropwise over 45 minutes to a suspension of 5-(1-hydroxycyclohexyl)-1-methyl-2(1H)-pyridinone (6.38 g) in 120 ml of acetonitrile at 0° C. The resulting solution was stirred at room temperature for 16 hours and then poured over ice, and the pH was adjusted to 8. The product was extracted into dichloromethane, and the combined organic layers were washed with brine, dried over magnesium sulfate, filtered and concentrated to afford a foam. Trituration with ethyl acetate afforded 6.3 g of powder. Recrystallization from isopropanol/diisopropyl ether gave 4.86 g of N-[1-(1,6-dihydro-1-methyl-6-oxo-3-pyridinyl)cyclohexyl]-acetamide as crystals, m.p. 194°–195° C.

ANALYSIS: Calculated for $C_{14}H_{20}N_2O_2$: 67.72%C; 8.12%H; 11.28%N. Found: 67.74%C; 8.12%H; 11.28%N.

EXAMPLE 12 cis-N-[1-(1,6-Dihydro-1-methyl-6-oxo-3-pyridinyl)-4-(1,1-dimethylethyl)cyclohexyl]acetamide Concentrated sulfuric acid (28 ml) was added dropwise over 45 minutes to stirred suspension of 5-[1-hydroxy-4-(1,1-dimethylethyl)cyclohexyl]-1-methyl-2(1H)-pyridinone (5.5 g) in 83 ml of acetonitrile at 0° C. The resulting solution was stirred at room temperature for 16 hours, and then it was poured over ice, and the pH was adjusted to 8. The product was extracted into dichloromethane, and the combined organic layers were washed with saturated sodium chloride solution, dried over magnesium sulfate, filtered and concentrated to leave 3.45 g of powder. Recrystallization from isopropanol/diisopropyl ether afforded 2.2 g of powder, m.p. 231°–232° C.

ANALYSIS: Calculated for $C_{18}H_{28}N_2O_2$: 71.02%C; 9.27%H; 9.20%N. Found: 70.68%C; 9.10%H; 9.13%N.

EXAMPLE 13

N-[1-[1,6-Dihydro-6-oxo-1-(phenylmethyl)-3-pyridinyl]-cyclohexyl]formamide hydrochloride Concentrated sulfuric acid (60 ml) was added dropwise over 30 minutes to a suspension of 5-(1-hydroxycyclohexyl-1-(phenylmethyl)-2(1H)-pyridinone (20.3 g) and potassium cyanide (14 g) in 290 ml of trifluoroacetic acid at 0° C. The resulting suspension was stirred at room temperature for 18 hours and then cooled to 0° C., and diethyl ether was added slowly. The solvent was decanted, and the solids were washed with diethyl ether. The product was then dissolved in methanol and neutralized with poly-4-vinylpyridine. The polymer was removed by filtration, and the filtrate concentrated to yield a foam. The product was converted to its HCl salt and used in subsequent reactions without further purification.

EXAMPLE 14

5-(1-Aminocyclohexyl)-2(1H)-pyridinone hydrochloride

A solution of N-[1-(1,6-dihydro-6-oxo-3-pyridinyl)-cyclohexyl]formamide hydrochloride (43.0 g) in 700 ml of methanol was heated at reflux for 17 hours, and then cooled and concentrated. The residual oil was triturated with methanol affording 13.1 g of a white powder. Recrystallization from methanol gave 5.5 g of crystals, m.p. 233°–234° C.

ANALYSIS: Calculated for $C_{11}H_{17}ClN_2O$: 57.77%C; 7.49%H; 12.25%N. Found: 57.89%C; 7.43%H; 12.26%N.

EXAMPLE 15

5-(1-Amino-4,4-dimethylcyclohexyl)-2(1H)-pyridinone hydrochloride

A solution of N-[1-(1,6-dihydro-6-oxo-3-pyridinyl)-4,4-dimethylcyclohexyl]formamide hydrochloride (7.05 g) in 125 ml of methanol was heated at reflux for 24 hours, and then the solution was cooled and concentrated in vacuo to a volume of 25 ml. The precipitated powder was collected, affording 3.07 g of analytically pure 5-(1-amino-4,4-dimethylcyclohexyl)-2(1H)-pyridinone hydrochloride, m.p. 229°–230° C.

ANALYSIS: Calculated for $C_{13}H_{20}N_2O \cdot HCl$: 60.81%C; 8.24%H; 10.91%N. Found: 60.42%C; 8.17%H; 10.83%N.

EXAMPLE 16

5-(1-Aminocyclohexyl)-1-methyl-2(1H)-pyridinone hydrochloride

Concentrated sulfuric acid (67 ml) was added dropwise over 45 minutes to a suspension of 5-(1-hydroxycyclohexyl)-1-methyl-2(1H)-pyridinone (17.2 g) and potassium cyanide (16.3 g) in 334 ml of trifluoroacetic acid at 0° C. The resulting suspension was stirred at room temperature for 18 hours, and then it was cooled to 0° C., and diethyl ether was added slowly. The solvent was decanted, and the solids were washed with diethyl ether. The product was then dissolved in methanol and neutralized with poly-4-vinylpyridine. The polymer was removed by filtration, and the filtrate concentrated to yield a foam. The foam was dissolved in methanol, acidified with ethereal hydrochloric acid and concentrated, affording 17.1 g of foam.

The product formed above was dissolved in 300 ml of methanol and heated at reflux for 16 hours. The resulting solution was cooled and concentrated in vacuo to a volume of 50 ml. The precipitated product was collect, affording 10.9 g of analytically pure product as a powder, m.p. 240°-245° C.

ANALYSIS: Calculated for $C_{12}H_{19}ClN_2O$: 59.38%C; 7.89%H; 11.54%N. Found: 59.12%C; 7.83%H; 11.51%N.

EXAMPLE 17

5-(1-Aminocyclohexyl)-1-(phenylmethyl)-2(1H)-pyridinone hydrochloride

A solution of N-[1-[1,6-dihydro-6-oxo-1-(phenylmethyl)-3-pyridinyl]-cyclohexyl]formamide hydrochloride (13.4 g) in 200 ml of methanol was heated at reflux for 17 hours. The mixture was cooled, and the resultant crystals were collected, affording 5.6 g of analytically pure 5-(1-aminocyclohexyl)-1-(phenylmethyl)-2(1H)-pyridinone hydrochloride, m.p. 248°-250° C. (dec).

ANALYSIS: Calculated for $C_{18}H_{23}ClN_2O$: 67.81%C; 7.27%H; 8.79%N. Found: 67.76%C; 7.20%H; 8.75%N.

EXAMPLE 18

N-[1-[6-(Benzoyloxy)-3-pyridinyl]cyclohexyl]benzamide

A solution of benzoic anhydride (13.9 g), triethylamine (11.6 g), 4-(N,N-dimethylamino)pyridine (0.17 g) and 5-(1-aminocyclohexyl)-2(1H)-pyridinone hydrochloride (6.15 g) in 100 ml of dichloromethane was stirred at room temperature for 4 hours. The resulting solution was diluted with dichloromethane, washed with water and brine, dried over magnesium sulfate, filtered, and concentrated to give 11.5 g of solid. Recrystallization from ethyl acetate/hexanes afford 5.6 g of product as needles, m.p. 167°-168.5° C.

ANALYSIS: Calculated for $C_{25}H_{24}N_2O_3$: 74.98%C; 6.04%H; 6.99%N. Found: 74.80%C; 6.08%H; 6.99%N.

EXAMPLE 19

N-[1-(1,6-Dihydro-6-oxo-3-pyridinyl)cyclohexyl]benzamide

A solution of N-[1-[6-(benzoyloxy)-3-pyridinyl]cyclohexyl]benzamide hydrochloride (10.4 g) was heated in 75 ml of refluxing methanol for 1 hour. The solution was cooled, and the solvent was removed in vacuo. The residual oil was triturated with a mixture of ethyl acetate and hexanes, affording 5.9 g of crude product as a solid. Recrystallization from isopropyl alcohol gave 1.91 g of a flocculent solid, m.p. 223°-224° C.

ANALYSIS: Calculated for $C_{18}H_{20}N_2O_2$: 72.95%C; 6.80%H; 9.45%N. Found: 72.85%C; 6.60%H; 9.73%N.

EXAMPLE 20

N-[1-(1,6-Dihydro-6-oxo-3-pyridinyl)cyclohexyl]acetamide

Sodium methoxide solution (25% in methanol, 6 ml) was added to a suspension of 5-(1-aminocyclohexyl)-2(1H)-pyridinone hydrochloride (6.0 g) in 100 ml of methanol, and the mixture was stirred at room temperature for 10 minutes. The solvent was removed in vacuo, and the residual solids were suspended in 260 ml of dichloromethane. Poly-4-vinylpyridine (5.42 g), acetic anhydride (2.67 g) and a catalytic amount of 4-(N,N-dimethylamino)pyridine were added, and the mixture was stirred at room temperature for 2 hours. The suspension was filtered and the solid residue was washed with methanol. The filtrate was concentrated, leaving 4.9 g of solid. Recrystallization from methanol gave 1.69 g of product (m.p. 238°-242° C. dec) in two crops, each of which was analytically pure.

ANALYSIS: Calculated for $C_{13}H_{18}N_2O$: 66.64%C; 7.74%H; 11.96%N. Found: 66.47%C; 7.69%H; 11.87%N.

EXAMPLE 21

N-[1-(1,6-Dihydro-6-oxo-3-pyridinyl)cyclohexyl]propionamide

A solution of propionic anhydride (8.89 g), triethylamine (13.8 g), 4-(N,N-dimethylamino)pyridine (47 mg) and 5-(1-aminocyclohexyl)-2(1H)-pyridinone hydrochloride (7.81 g) in 170 ml of dichloromethane was stirred at room temperature for 4 hours. The resulting mixture was diluted with water and extracted with dichloromethane. The combined organic layers were washed with saturated sodium bicarbonate solution and brine, dried over magnesium sulfate, filtered and concentrated to give 6.1 g of a solid. Recrystallization from ethanol gave 4.6 g of product as crystals, m.p. 227°-228° C.

ANALYSIS Calculated for $C_{14}N_{20}N_2O_2$: 67.72%C; 8.12%H; 11.28%N. Found: 67.42%C; 8.18%H; 11.18%N.

EXAMPLE 22

N-1-[1,6-Dihydro-1-methyl-6-oxo-3-pyridinyl]cyclohexyl]-benzeneacetamide

Phenylacetic acid (4.2 g) was added to a solution of carbonyl diimidazole (5.1 g) in 280 mL of dichloromethane at room temperature. The resulting solution was stirred for 1 hour, and then triethylamine (3.2 g) and 5-(1-aminocyclohexyl)-1-methyl-2(1H)-pyridinone hydrochloride (6.9 g) were added sequentially. The resulting suspension was stirred at room temperature for 16 hours, and then water was added, and the layers were separated. The aqueous phase was extracted with ethyl acetate, and the combined organic layers were washed with saturated sodium chloride solution, dried over magnesium sulfate, filtered, and concentrated to afford 6.1 g of solid. The product was recrystallized twice from isopropanol to give 1.68 g of product as crystals, m.p. 221°-223° C.

ANALYSIS: Calculated for $C_{20}H_{24}N_2O_2$: 74.05%C; 7.46%H; 8.63%N. Found: 73.69%C; 7.64%H; 8.49%N.

EXAMPLE 23

N-[1-[1,6-Dihydro-6-oxo-1-(phenylmethyl) -3-pyridinyl]-cyclohexyl]-benzeneacetamide Phenylacetyl chloride (1.6 g) was added to a well stirred suspension of 5-(1-aminocyclohexyl)-1-(phenylmethyl)-2(1H)-pyridinone (2.9 g), poly-4-vinylpyridine (2.1 g) and a catalytic amount of 4-(N,N-dimethylamino)pyridine in 70 ml of dichloromethane, and the resulting mixture was stirred at room temperature for 3 hours. The reaction mixture was filtered and the filtrate concentrated to give 4.1 g of oil. Column chromatography (silica gel, elution with ethyl acetate) afforded 2.1 g of foam. Recrystallization from ethyl acetate/hexanes gave 1.7 g of analytically pure product as needles, m.p. 152°-153° C.

ANALYSIS: Calculated for $C_{26}H_{28}N_2O_2$: 77.97%C; 7.05%H; 6.99%N. Found: 77.97%C; 7.07%H; 6.96%N.

EXAMPLE 24

N-[1-(1,6-Dihydro-6-oxo-3-pyridinyl)cyclohexyl]-chloroacetamide

Triisopropylsilyl trifluoromethane sulfonate (9.98 g) was added dropwise to a suspension of 5-(1-aminocyclohexyl)-2-(1H)-pyridinone (6.26 g) and 2,6-lutidine (3.49 g) in 330 mL of dichloromethane. The resulting mixture was stirred at room temperature for 2 hours and then poured into water. The layers were separated, and the aqueous phase was extracted with dichloromethane. The combined organic layers were washed with water and brine, dried over $MgSO_4$ and concentrated to give 9.66 g of oil.

A portion of the product formed above (7.83 g) was combined with 4.5 g of poly-4-vinylpyridine, chloroacetic anhydride (3.8 g) and a catalytic amount of 4-(N,N-dimethylamino)pyridine in 100 mL of dichloromethane. The mixture was stirred for 2 hours and then filtered. The filtrate was concentrated, affording 1.9 g of product as a solid.

EXAMPLE 25

N-[1-(1,6-Dihydro-6-oxo-3-pyridinyl)cyclohexyl]-[4-(4-fluorobenzoyl)]-1-piperidineacetamide A mixture of N-[1-(1,6-dihydro-6-oxo-3-pyridinyl)cyclohexyl]chloroacetamide (1.74 g), 4-(4-fluorobenzoyl)-piperidine hydrochloride (1.57 g) and diisopropylethylamine (1.67 g) was heated in 35 ml of refluxing acetonitrile for 1 hour. The resulting suspension was cooled to room temperature and the solid was collected, yielding 1.8 g of solid. Recrystallization from methanol gave 1.1 g of product as a solid, m.p. 243°–245° C. (dec).

ANALYSIS: Calculated for $C_{25}H_{30}FN_3O_3$: 68.32%C; 6.88%H; 9.56%N. Found: 68.23%C; 7.07%H; 9.57%N.

EXAMPLE 26

5-[1-(Methylamino)cyclohexyl]-1-methyl-2(1H)-pyridinone dihydrochloride

A solution of acetic acid (25.0 g) in 70 ml of tetrahydrofuran was added dropwise over 1 hour to a mechanically stirred suspension of sodium borohydride (1.58 g) and N-[1-[1,6-dihydro-1-methyl-6-oxo-3-pyridinyl]cyclohexyl]-formamide (20.0 g) in 420 ml of tetrahydrofuran at 0° C. The resulting mixture was heated to reflux and stirred at that temperature for 17 hours. The reaction mixture was cooled to room temperature, and the solvent was removed in vacuo. The residue was quenched with water, and the product was extracted into dichloromethane. The combined organic layers were dried over magnesium sulfate, filtered, and concentrated to provide 12.7 g of oil. Purification by column chromatography on silica gel (elution with triethylamine/methanol/ethyl acetate) afforded 6.5 g of product as an oil, which was dissolved in methanol and acidified with ethereal HCl. The solvent was removed in vacuo, and the product crystallized from ethanol/ethyl acetate. Two recrystallizations from ethanol provided 3.3 g of an analytically pure solid, m.p. 190°–191.5° C.

ANALYSIS: Calculated for: 53.25%C; 7.56%H; 9.55%N. Found: 53.22%C; 7.70%H; 9.50%N.

EXAMPLE 27

5-[1-(Methylamino)cyclohexyl]-1-(phenylmethyl)-2(1H)-pyridinone fumarate

A solution of acetic acid (19.86 g) in 50 ml of tetrahydrofuran was added dropwise over 1 hour to a mechanically stirred suspension of sodium borohydride (12.3 g) and N-[1-[1,6-dihydro-1-(phenylmethyl)-6-oxo-3-pyridinyl]-cyclohexyl]formamide (20.4 g) in 328 ml of tetrahydrofuran at 0° C. The resulting mixture was heated to reflux and stirred at that temperature for 17 hours. The reaction mixture was cooled to room temperature, and the solvent was removed in vacuo. The residue was quenched with water, and the product was extracted into dichloromethane. The combined organic layers were dried over magnesium sulfate, filtered, and concentrated to provide 14.5 g of oil. Purification by HPLC on silica gel (elution with triethylamine/methanol/ethyl acetate) afforded 7.5 g of product as an oil. A portion of the product (4.3 g) was dissolved in hot ethyl acetate, and an equivalent amount of fumaric acid in hot methanol was added to the solution. The solution was allowed to cool, and the resultant crystals were collected to afford 5.2 g of analytically pure material, m.p. 184°–185° C.

ANALYSIS: Calculated for: 66.97%C; 6.84%H; 6.79%N. Found: 66.91%C; 6.86%H; 6.77%N.

EXAMPLE 28

N-[1-[1,6-Dihydro-6-oxo-1-(2-propynyl)-3-pyridinyl]-cyclohexyl]formamide

A well stirred mixture of N-[1-(1,6-dihydro-6-oxo-3-pyridinyl)-cyclohexyl]formamide (13.8 g), 3-bromo-1-trimethylsilyl-1-propyne (8.87 g) and potassium carbonate (17.3 g) in 250 mL of dimethylformamide was kept at room temperature for 18 hours. The mixture was filtered, and the solvent was removed in vacuo, leaving 16.2 g of solid.

A portion of the compound prepared above (12.1 g) was dissolved in 150 mL of tetrahydrofuran at 0° C. and treated dropwise with tetra-n-butylammonium fluoride (1M in tetrahydrofuran, 36.1 mL). The resulting solution was stirred for 0.5 hour and then poured into water. The aqueous phase was separated and extracted with ethyl acetate. The combined organic layers were dried over $MgSO_4$ and concentrated to give 6.8 g of crude product. This was combined with an additional 3.3 g obtained as above, and purified via HPLC on silica gel (elution with methanol/ethyl acetate) to give 7.2 g of pure compound.

EXAMPLE 29

5-(1-Aminocyclohexyl)-1-[4-(pyrrolidin-1-yl)-2-butynyl]-2(1H)-pyridinone

Copper (I) chloride (0.9 g) was added in one portion to a mixture of N-[1-[1,6-dihydro-6-oxo-1-(2-propynyl)-3-pyridinyl]-cyclohexyl]formamide (6.7 g), paraformaldehyde (0.94 g) and pyrrolidine (2.2 g) in 26 mL of dioxane. The resulting solution was stirred at room temperature for 2 hours, and then it was acidified with 10% HCl solution. The aqueous layer was separated, extracted with dichloromethane, and basified with $Na_2CO_3(s)$. The product was extracted into dichloromethane, and the combined organic layers were dried over magnesium sulfate, filtered, and concentrated to afford an oil. The crude product was deposited on silica gel (35 g) and filtered through a pad of silica gel (elution with 20% methanol/80% ethyl acetate). Concentration of the filtrate afforded 6.02 g of product. A portion of the product (5.42 g) was dissolved in methanol and acidified with etheral HCl. The resulting foam was used in the subsequent reaction without further purification.

The hydrochloride (15.9 mmol) formed above was dissolved in 90 mL of methanol, and the resulting solution was heated at reflux for 16 hours. The solution was cooled, and the solvent was removed in vacuo. The residue was basified with saturated NaHCO$_3$ solution, and the product was extracted into dichloromethane. The combined organic layers were dried over K$_2$CO$_3$, filtered, and concentrated to give 4.3 g of crude product, which was filtered through silica gel (elution with ethyl acetate) to provide 4.0 g of product as a solid. Recrystallization from ethyl acetate/hexanes gave 1.9 g of analytically pure product, m.p. 97°–99° C.

ANALYSIS: Calculated for C$_{19}$H$_{27}$N$_3$O: 72.81%C; 8.68%H; 13.41%N. Found: 72.69%C; 8.59%H; 13.28%N.

We claim:

1. A compound having the formula,

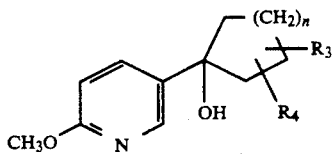

where
n is 1, 2 or 3;
R$_3$ is hydrogen or loweralkyl; and
R$_4$ is hydrogen or loweralkyl.

2. The compound as defined in claim 1, where R$_3$ and R$_4$ are both hydrogen.

3. The compound as defined in claim 1, where n is 2.

4. The compound as defined in claim 1, which is 5-(1-hydroxycyclohexyl)-2-methoxypyridine.

5. The compound as defined in claim 1, which is 5-[4-(1,1-dimethylethyl)-1-hydroxycyclohexyl]-2-methoxypyridine.

* * * * *